United States Patent [19]
Oku et al.

[11] Patent Number: 6,046,369
[45] Date of Patent: Apr. 4, 2000

[54] PROCESS FOR PRODUCING α-PHENYLETHYL ALCOHOL

[75] Inventors: Noriaki Oku, Ichihara; Masaru Ishino, Sodegaura, both of Japan

[73] Assignee: Sumitomo Chemical Co., Ltd., Osaka, Japan

[21] Appl. No.: 09/113,294

[22] Filed: Jul. 10, 1998

[30] Foreign Application Priority Data

Jul. 14, 1997 [JP] Japan ................................. 9-188182
Dec. 15, 1997 [JP] Japan ................................. 9-344732

[51] Int. Cl.⁷ .................................................. C07C 29/145
[52] U.S. Cl. ........................................... 568/814; 568/715
[58] Field of Search ..................... 568/814, 715

[56] References Cited

U.S. PATENT DOCUMENTS

| 3,927,120 | 12/1975 | Grane et al. |
|---|---|---|
| 3,927,121 | 12/1975 | Grane et al. |
| 4,160,746 | 7/1979 | Rashkin. |
| 4,208,539 | 6/1980 | Rashkin. |
| 4,996,374 | 2/1991 | Lin et al. ................ 568/814 |
| 5,663,458 | 9/1997 | Ito et al. ................ 568/814 |

FOREIGN PATENT DOCUMENTS

| 0 604 792 | 7/1994 | European Pat. Off. |
|---|---|---|
| 0 714 877 | 6/1996 | European Pat. Off. |
| 39 33 661 | 4/1991 | Germany. |
| 59-27216 | 7/1984 | Japan. |
| 8-198788 | 8/1996 | Japan. |
| 2 269 116 | 2/1994 | United Kingdom. |

OTHER PUBLICATIONS

Patent Abstracts of Japan, vol. 14, No. 37 (C–680), published Jan. 24, 1990 (corresponds to JPA 1–272540, published Oct. 31, 1989).

Patent Abstracts of Japan, vol. 14, No. 270 (C–727), published Jun. 12, 1990 (Corresponds to JPA 2–78639, published Mar. 19, 1990).

Patent Abstracts of Japan, vol. 14, No, 254 (C–724), published May 31, 1990 (corresponds to JPA 2–73027, published Mar. 13, 1990).

*Primary Examiner*—Michael G. Ambrose
*Attorney, Agent, or Firm*—Sughrue, Mion, Zinn, Macpeak & Seas, PLLC

[57] ABSTRACT

A process for producing α-phenylethyl alcohol, which comprises hydrogenating acetophenone by a fixed bed flow reaction in the presence of a catalyst, wherein the reaction is conducted in the state where the liquid hold up ratio in a reactor is in the range of from 30% to 90%.

10 Claims, No Drawings

PROCESS FOR PRODUCING α-PHENYLETHYL ALCOHOL

BACKGROUND OF THE INVENTION

The present invention relates to a process for producing α-phenylethyl alcohol. More particularly, the present invention relates to a process for producing α-phenylethyl alcohol in which acetophenone is hydrogenated by a fixed bed flow reaction in the presence of a catalyst, wherein the amount of ethylbenzene produced as a by-product is controlled at a sufficiently low level, and hence the selectivity for α-phenylethyl alcohol is high, thus the process being extremely excellent in an industrial production.

The α-phenylethyl alcohol is useful as, for example, a starting material for producing styrene, and materials for producing various kinds of perfumes. It is known that α-phenylethyl alcohol can be produced by the hydrogenation of acetophenone. For example, in Japanese Patent Publication No.59-27216, there is disclosed a process for hydrogenating acetophenone by using copper-chromite catalyst containing barium, zinc, and magnesium. However, there had not been previously known that a process for producing α-phenylethyl alcohol by hydrogenating acetophenone in a fixed bed with high selectivity and efficiency.

SUMMARY OF THE INVENTION

Under these circumstances, an object of the present invention is to provide a process for producing α-phenylethyl alcohol in which acetophenone is hydrogenated by a fixed bed flow reaction in the presence of a catalyst, i.e., a process for producing α-phenylethyl alcohol extremely excellent in an industrial production, wherein productivity per unit volume of a reactor is high even under low pressure (the reaction efficiency is high), and the amount of ethylbenzene produced as a by-product is controlled at a sufficiently low level, resulting in high selectivity for α-phenylethyl alcohol That is, the present invention is to provide a process for producing α-phenylethyl alcohol, which comprises hydrogenating acetophenone by a fixed bed flow reaction in the presence of a catalyst, wherein the reaction is conducted in the state where the liquid hold up ratio in a reactor is in the range of from 30% to 90%.

It is difficult to proceed the reaction of the hydrogenation of acetophenone in general because the reaction rate of the hydrogenation of acetophenone is slower than that of the other hydrogenation reaction such as olefin. Accordingly, the hydrogenation reaction of acetophenone has been conducted industrially under high pressure and a large amount of hydrogen. The liquid feed must be also diluted by the other solvent that enables hydrogen gas to dissolve in liquid phase. In these cases, the running and equipment cost are high due to an increase in equipment for recycling excess hydrogen and the solvent for the dilution of feed. The applicants have found that the reaction rate strongly depends on the ratio of a reaction liquid (containing acetophenone) to a reaction gas in a reactor (catalyst charged layer) by an analysis of the acetophenone hydrogenation rate in detail.

With respect to the hydrogenation reaction, the acetophenone in a liquid is allowed to react with dissolved hydrogen on a catalyst, wherein the hydrogen consumed in the liquid is supplied from a gas phase. In the present invention, the reaction is carried out under the conditions of holding larger liquid hold up than that of the conventional process, resulting in longer liquid residence time in the catalyst bed and the larger amount of dissolved hydrogen. Consequently, high reaction efficiency can be achieved, resulting in high acetophenone conversion ratio and small yield of by-product ethylbenzene even under lower pressure than the conventional process. When the liquid hold up is too low, the reaction efficiency decreases. On the other hand, when it is too large, the gas hold up extremely decreases and it is impossible to supply hydrogen gas from the gas phase effectively to become the reaction efficiency worse. It has been found that running at most suitable liquid hold up ratio can maintain the reaction efficiency at high level, completing the present invention.

In the hydrogenation reaction of the fixed bed reaction system of the present invention, effective removal of heat of reaction is particularly important in maintaining the reaction selectivity at high level. In the hydrogenation reaction of acetophenone, excessive hydrogenation reaction results in the formation of ethylbenzene. Accordingly, it has great industrial significance to produce α-phenylethyl alcohol by limiting the amount of ethylbenzene as small as possible. The analysis of the reaction results indicate that the formation of ethylbenzene greatly depends on the reaction temperature, and significantly increases at a temperature of over 150° C. The reaction heat of the hydrogenation of acetophenone to α-phenylethyl alcohol is about 50 KJ per 1 mol of acetophenone. When the liquid hold up ratio in a reactor is too small, insufficient removal of reaction heat in the reactor results in the formation of heat spots to produce much amount of ethylbenzene as a by-product, and the reaction selectivity becomes worse. Under these circumstances, the inventors has found that the amount of ethylbenzene produced as a by-product can be controlled by setting the liquid hold up ratio in a reactor at a prescribed amount resulting in maintaining high conversion ratio of acetophenone. The liquid hold up ratio in a reactor is determined depending upon the amount of liquid and the amount of gas per sectional area of the reactor. The liquid hold up ratio in a reactor is in the range of from 30% to 90%, preferably in the range of from 40% to 70% so as to control the amount of ethylbenzene produced as a by-product.

The terms "liquid hold up" and "liquid hold up ratio" in the present invention are defined as follows:

The amount of liquid capable of filling the inside of a reactor after charging a catalyst into the reactor is taken as 100. The amount of liquid staying in the reactor at the time when a material gas and material liquid are actually flown therein to reach the steady state is defined as liquid hold up. The value expressed as the ratio to the above described 100 is defined as liquid hold up ratio. For example, the liquid hold up and liquid hold up ratio can be determined as follows: a prescribed gas and liquid are supplied into a reactor to ensure the steady state, after which the valves each provided at the inlet and outlet of the reactor, respectively, are stopped at the same time. Then, the amount of liquid remaining in the reactor is drawn to be measured. However, the measuring method is not limited thereto. The liquid hold up can be changed into the desired amount by appropriately selecting the amounts of gas and liquid to be fed into the reactor, and the size of the reactor.

The catalyst usable in the present invention is the one which allows acetophenone to be hydrogenated to produce α-phenylethyl alcohol. Examples of which said catalyst include copper-based catalysts, and noble metal catalysts. Examples of the copper-based catalyst include catalysts disclosed in Japanese Patent Publication No. 59-27216, EPO No. 714877, and DE No.3933661, but do not limit to these catalyst. These catalysts mean the catalysts containing CuO as a main component. The content of CuO in a catalyst is generally in the range of from 10% to 90 wt %, preferably in the range of from 20% to 80 wt %. Even if the content is too high or too low, hydrogenation activity may become low. Examples of components other than CuO in a catalyst include various kinds of metal oxides such as $Cr_2O_3$, ZnO, $FeO_3$, $Al_2O_3$, $La_2O_3$, $Sm_2O_3$, $CeO_2$, $Zro_2$, $TiO_2$, $MnO_2$, $Co_2O_3$, NiO, $SiO_2$, BaO, CaO, and MgO. Specifically, catalysts of the mixed oxides with silica are preferable. Further, an alkali metal compound may be contained as a component other than the above-described ones. Examples of the noble metal type catalysts include catalysts containing Pd, Rh, Pt, and Ru. Examples of these include catalysts disclosed in U.S. Pat. No. 4,996,374, Japanese Patent Publication No. 1-272540, and Japanese Patent Publication No. 2-78639, but do not limit to these catalysts.

The catalyst of the present invention may be supported on a carrier. Examples of the carrier include metal oxides such as silica, alumina, titania, zirconia, magnesia, and silica-alumina, and mixed oxides thereof; bentonite, monmorillonite, diatomaceous earth, and acid clay. Among them, silica and diatomaceous earth are preferable. Binders such as graphite, silica sol, and aluminamaybe added in molding a catalyst.

The catalyst is preferably a molded pellet with a diameter of 3 mm or less, preferably of 2 mm or less. When the catalyst is too large, the reaction may not proceed to a sufficient degree, or the amount of ethylbenzene produced as a by-product may increase. The lower limit of the diameter of the catalyst is not specifically limited. However, it is preferable that the diameter of the catalyst is 1 mm or more in terms of controlling the pressure drop in the catalyst bed. Examples of the shape of the catalyst include spheroidal or cylindrical shape and the like. In the case of cylindrical shape, said diameter represents the diameter of the sectional circle. In the cases of other shapes, said diameter means the maximum diameter of the section In the case of the cylindrical shape, the height of the cylindrical shape is not specifically limited, however it is generally in the range of from 1 mm to 10 mm The catalyst of the present invention can be produced by a coprecipitation method, precipitation method, mixing method, and the like. For example, paste obtained by the coprecipitation method is heated to obtain catalyst powder. The aforementioned binder and the like are added to said catalyst powder to obtain a molded pellet by tabletting molding or extrusion molding. The commercially available catalysts can be also employed.

The hydrogenation reaction of acetophenone is carried out by the use of a fixed bed flow reactor charged with the above-mentioned catalyst. This method requires no filtration of catalyst powder from a reaction liquid and hence it is more excellent method in terms of industrial production as compared with a slurry reaction method using powder catalyst. The reaction temperature is generally in the range of from 40° C. to 200° C., preferably in the range of from 60° C. to 150° C. The reaction pressure is generally in the range of from 1 MPa to 20 MPa. It becomes possible to react under lower pressure of from 1 MPa to 5 MPa in the present invention. The reaction under lower pressure becomes possible, so the method of the present invention has great industrial significance in terms of a reduction in equipment cost and improvement in safety. Excessive low temperature or low pressure may inhibit the proceeding of the reaction to a sufficient degree. On the other hand, excessive high temperature or high pressure may cause not only increase of equipment cost and maintenance cost, but also increase of the amount of ethylbenzene produced as a by-product. The amount of catalyst to be used is generally in the range of from 0.01 $hr^{-1}$ to 50 $hr^{-1}$, preferably in the range of from 0.1 $hr^{-1}$ to 20 $hr^{-1}$ as space velocity of a material liquid to a catalyst bed. The amount of hydrogen to be supplied is generally in the range of from 1.0 to 3 times as much as the amount of acetophenone in the material liquid to be fed on a mole basis.

The hydrogen and material liquid may be supplied by up flow or down flow if the liquid hold up ratio is in the range of from 30% to 90%. In the case of up flow, the liquid phase becomes continuous phase in a catalyst bed by its own weight of the material liquid, and hydrogen gas flows therein as bubbles. Accordingly, there is no danger of entailing the following situation as in the case of down flow: the dispersion of the liquid becomes uneven, resulting in an increase of the amount of ethylbenzene produced as a by-product, runaway of the reaction, and a decrease of catalyst activity due to a local temperature rise. In the case of down flow, the liquid hold up ratio in a reactor changes depending on the liquid space velocity and gas space velocity, resulting in variations in reaction results. On the other hand, in the case of up flow, the liquid is a continuous phase in the reactor, and hence it is difficult for the variations as described above to arise.

As a raw material for the reaction, only acetophenone may be used, however, mixed liquid containing impurities and the like other than acetophenone may be also used. A solution with an adequate solvent being added therein may be used. Examples of the solvent include alcohols such as methanol, ethanol, propanol, ethylene glycol monomethyl ether, and α-phenylethyl alcohol; ethers such as diethyl ether, tetrahydrofran, dioxane, and ethylene glycol dimethyl ether; hydrocarbons such as hexane, heptane, toluene, and ethylbenzene; and mixed solvent thereof. The amount of solvent to be used is generally in the range of from 0.5 to 10 times that of acetophenone on a weight basis. Such dilution of acetophenone material is effective in maintaining the selectivity of the reaction at high level.

In the fixed bed flow hydrogenation reaction of the present invention, a part of the reaction liquid after hydrogenation reaction may be recycled in a material liquid for hydrogenation reaction. The recycling of a part of the reaction liquid enables the effective removal of reaction heat, and hence it is effective in maintaining the selectivity of the reaction at high level.

According to the present invention, it becomes possible to provide a method for producing α-phenylethyl alcohol by a fixed bed flow reaction, extremely excellent in terms of industrial production, wherein the amount of ethylbenzene produced as a by-product is controlled at sufficiently low level, resulting in high selectivity for α-phenylethyl alcohol.

DETAILED DESCRIPTION OF THE PREFERRED EMBODIMENTS

EXAMPLES

The present invention will be described by way of examples, which should not be construed as limiting the scope of the invention.

Example 1

In a fixed bed adiabatic reactor, which is a tube(inner diameter of 4.1 cm and length of catalyst bed of 78 cm) fixed vertically, a copper-silica pellet catalyst (1 litter) (containing 63 wt % CuO, 1.5 mm φ×4 mmL) is charged. Then, a fresh material liquid containing 56 wt % of acetophenone (hereinafter, referred to as "ACP"), 16 wt % of α-phenylethyl alcohol (hereinafter, referred to as "MBA"), 0.04 wt % of ethylbenzene (hereinafter, referred to as "EB"), and 28 wt % of the other compounds at a rate of 1l/hr, and mixed gas made of 84 volume % of hydrogen and 16 volume % of methane at a rate of 0.3 Nm$^3$/hr on a normal state basis (the mole ratio of hydrogen to material acetophenone is 2.4 times on a mole basis) were supplied therein by up flow to conduct a hydrogenation reaction at 24 kg/cm$^2$G. In this step, a part of the hydrogenation reaction liquid at the outlet of the reactor was recycled to the inlet of the reactor. In the steady state (after making sure of a material balance), the valve provided at the inlet and outlet of the reactor were closed at the same time, liquid remaining in the reactor was drawn out to be measured. Then, the liquid hold up ratio was calculated and the value was 50%. The inlet temperature was controlled at 94° C., then the outlet temperature was 116° C. The reaction results determined from the composition of the inlet and outlet of the reactor were as follows: the ACP conversion ratio was 96%, while the EB selectivity ratio was 1.7%.

Example 2

The experiment was carried out in the same manner as in example 1, except that a fresh material liquid and hydrogen gas were supplied into a reactor by down flow, and liquid hold up ratio was adjusted to be set at 35%. The temperatures at the reactor inlet and outlet in steady state were found to be 109° C. and 118° C., respectively. The reaction results determined from the composition of the inlet and outlet of the reactor were as follows: the ACP conversion ratio were 94%, and the EB selectivity ratio was 1.8%.

Example 3

The experiment was carried out in the same manner as in example 1, except that the catalyst volume was 2l(the height of the catalyst bed was 148 cm), and that a fresh material liquid containing 46 wt % of ACP, 20 wt % of MBA, and 34 wt % of the other compounds at a rate of 2l/hr, and mixed gas made of 84 volume % of hydrogen and 16 volume % of methane at a rate of 1.8 Nm$^3$/hr were supplied therein. The inlet temperature was controlled at 84° C., then the outlet temperature was 119° C. The reaction results determined from the composition of the inlet and outlet of the reactor were as follows: the ACP conversion ratio was 96%, while the EB selectivity ratio was 1.7%.

Comparative Example 1

The experiment was carried out in the same manner as in example 2, except that the liquid hold up ratio was set at 25%, and that a fresh material liquid containing 52 wt % of ACP, 18 wt % of MBA, 0.04 wt % of EB, and 30 wt % of the other compounds was supplied. The inlet temperature was controlled at 102° C., then the outlet temperature was 115° C. The reaction results determined from the composition of the inlet and outlet of the reactor were as follows: the ACP conversion ratio was 92% while the EB selectivity ratio was 2.6%.

What is claimed is:

1. A process for producing α-phenylethyl alcohol, which comprises hydrogenating acetophenone by a fixed bed flow reaction in the presence of a catalyst, wherein the reaction is conducted in the state where the liquid hold up ratio in a reactor is in the range of from 30% to 50%.

2. The process according to claim 1, wherein the reaction is conducted in the state where the liquid hold up ratio in a reactor is in the range of from 35% to 50%.

3. The process according to claim 1, wherein the catalyst is a copper-based catalyst.

4. The process according to claim 1, wherein the catalyst is a molded pellet with a diameter of 3 mm or less.

5. The process according to claim 1, wherein the catalyst is a molded pellet with a diameter of 2 mm or less.

6. The process according to claim 1, wherein the reaction is conducted at a pressure of 1 Mpa to 5 MPa.

7. The process according to claim 1, wherein the reaction is conducted at a reaction temperature of 60° C. to 150° C.

8. The process according to claim 1, wherein the reaction is conducted under the conditions of the mole ratio of hydrogen to acetophenone is in the range of from 1 to 3.

9. The process according to claim 1, wherein a part of a reaction liquid after reaction is recycled to the inlet of the reactor.

10. The process according to claim 1, wherein a liquid feed to be supplied to the reactor is carried out by up flow.

* * * * *